United States Patent
Hughes et al.

(10) Patent No.: US 8,481,781 B2
(45) Date of Patent: *Jul. 9, 2013

(54) FORMULATIONS OF CANFOSFAMIDE AND THEIR PREPARATION

(75) Inventors: Betsy R. Hughes, Mountain View, CA (US); Robert Steven Lopez, Truckee, CA (US)

(73) Assignee: Telik, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/069,239

(22) Filed: Mar. 22, 2011

(65) Prior Publication Data

US 2011/0224175 A1 Sep. 15, 2011

Related U.S. Application Data

(63) Continuation of application No. 12/511,245, filed on Jul. 29, 2009, now abandoned.

(60) Provisional application No. 61/092,580, filed on Aug. 28, 2008.

(51) Int. Cl.
*C07C 229/00* (2006.01)

(52) U.S. Cl.
USPC .................................................. 562/448

(58) Field of Classification Search
None
See application file for complete search history.

(56) References Cited

U.S. PATENT DOCUMENTS

| | | |
|---|---|---|
| 4,931,441 A | 6/1990 | Lawrence |
| 6,323,193 B1 | 11/2001 | Somani et al. |
| 6,403,098 B1 | 6/2002 | Burke et al. |
| 2006/0135409 A1 | 6/2006 | Boulanger et al. |
| 2006/0286037 A1 | 12/2006 | Hirano et al. |
| 2007/0082838 A1 | 4/2007 | De et al. |
| 2012/0015892 A1 | 1/2012 | Hughes et al. |

FOREIGN PATENT DOCUMENTS

| | | |
|---|---|---|
| WO | WO2006/068769 | 6/2006 |
| WO | WO-2010/025011 A1 | 3/2010 |

OTHER PUBLICATIONS

McIntyre JA and J Castaner, "Canfosfamide Hydrochloride," Drugs Fut., 29(10), 985-991 (2004).
Morgan et al., "Tumor efficacy and bone marrow-sparing properties of TER286, A cytotoxin activated by glutathione S-transferase" Cancer Research, 58(12) pp. 2568-2575 (1998).
Tew KD, "TLK-86; a novel glutathione S-transferase-activated prodrug," Expert Opin. Investig. Drugs, 14(8), 1047-1054 (2005).
International Search Report for PCT/US2009/052694, dated Nov. 1, 2011.
International Search Report for PCT/US2011/026303, dated Nov. 14, 2011.

*Primary Examiner* — Susanna Moore
*Assistant Examiner* — Jennifer C Sawyer
(74) *Attorney, Agent, or Firm* — Foley & Lardner LLP

(57) ABSTRACT

Formulations of canfosfamide and their preparation.

4 Claims, No Drawings

FORMULATIONS OF CANFOSFAMIDE AND THEIR PREPARATION

CROSS-REFERENCE TO RELATED APPLICATION

This application claims priority to and is a continuation of U.S. application Ser. No. 12/511,245, filed 29 Jul. 2009, which is now abandoned, which claims the priority under 35 U.S.C. 119(e) of U.S. Provisional Application No. 61/092,580, filed 28 Aug. 2008, each of which are hereby incorporated by reference in their entirety in this application.

BACKGROUND OF THE INVENTION

1. Field of the invention

This invention relates to formulations of canfosfamide and their preparation.

2. Description of the related art

McIntyre and Castañer, "Canfosfamide Hydrochloride", *Drugs Fut.*, 29 (10), 985-991 (2004), describe canfosfamide hydrochloride (USAN), a phosphorodiamidate anticancer agent activated by glutathione S-transferase P1-1. The article also identifies canfosfamide hydrochloride with the codes TER-286 and TLK-286.

Morgan et al., "Tumor Efficacy and Bone Marrow-sparing Properties of TER286, a Cytotoxin Activated by Glutathione S-Transferase", *Cancer Research*, 58 (12), 2568-2575 (1998) describe preclinical studies on canfosfamide hydrochloride, including animal studies. According to the article, "for some studies, it was prepared in 60 mM sodium citrate for i.v. delivery."

Tew et al., "TLK-286: a novel glutathione S-transferase-activated prodrug", *Expert Opin. Investig. Drugs*, 14 (8), 1047-1054 (2005), note that "The formulation of TLK-286 in vials containing 265 mg of the sterile lyophilized drug permits solubilization in water for injection to a concentration of 50 mg/ml, followed by dilution to the appropriate dose in 5% dextrose for injection."

The disclosures of the documents referred to in this application are incorporated into this application by reference.

SUMMARY OF THE INVENTION

In a first aspect, this invention is a formulation of canfosfamide consisting essentially of (50±5) mg/mL canfosfamide hydrochloride in (100±10) mM sodium citrate buffer at pH 4.6±0.2.

In a second aspect, this invention is a method of preparing the formulation of the first aspect of this invention.

In a third aspect, this invention is a lyophilized formulation prepared by lyophilizing the formulation of the first aspect of this invention.

In a fourth aspect, this invention is a method of preparing the lyophilized formulation of the third aspect of this invention.

DETAILED DESCRIPTION OF THE INVENTION

Definitions

"Consisting essentially of" is a term of limitation and means to include the presence of stated components, groups, steps, and the like and to exclude the presence of others that materially alter the basic characteristics of what is being claimed or described. Thus a formulation consisting essentially of canfosfamide hydrochloride contains canfosfamide hydrochloride and not another active ingredient or another salt of canfosfamide except for incidental impurities. "Comprising" is a term of inclusion and not of limitation and means to include the presence of stated components, groups, steps, and the like but not to exclude the presence or addition of other components, groups, steps, and the like. Unless the context clearly requires otherwise, the singular includes the plural; so that, for example, "a sodium salt of citric acid" includes both a single such salt and two or more such salts.

A "sodium citrate buffer" is a solution consisting essentially of a sodium salt of citric acid, and optionally citric acid, dissolved in water, typically at a stated pH.

Because the formulation of this invention contains salts dissolved in water, it will necessarily contain dissociated ions as well as non-ionized species. Accordingly, describing the formulation as consisting essentially of canfosfamide hydrochloride in sodium citrate buffer does not describe the association of canfosfamide with hydrochloric acid, or a particular state of ionization of the canfosfamide (which has an amine and two carboxylate groups), or the association of sodium ions with citrate/hydrogen citrate/dihydrogen citrate ions, or other associations or ionization states, but rather that the formulation contains the product of the dissolution of the stated ingredients at the stated concentration in water at the stated pH.

The Formulation

In a first aspect, this invention is a formulation of canfosfamide consisting essentially of (50±5) mg/mL canfosfamide hydrochloride in (100±10) mM aqueous sodium citrate buffer at pH 4.6±0.2.

In a second aspect, this invention is a method of preparing the formulation of the first aspect of this invention. The method comprises:

(a) preparing aqueous sodium citrate buffer at pH 6.5±0.1,
(b) dissolving canfosfamide hydrochloride in the buffer,
(c) if necessary, adjusting the pH of the resulting solution to pH 4.6±0.2.

The aqueous sodium citrate buffer may be prepared by the dissolution of one or more sodium citrate salts, and optionally citric acid, for example trisodium citrate dihydrate and citric acid monohydrate, in water, followed if necessary by an adjustment of the pH to the desired value of 6.5±0.1 by the addition of an acid, such as 1 M hydrochloric acid, or a base, such as 1 M sodium hydroxide.

The canfosfamide hydrochloride is added to the buffer and stirred to achieve dissolution. The addition of the canfosfamide hydrochloride to the buffer will reduce the pH of the mixture to approximately 4.6±0.2, or slightly higher; and the pH of the mixture may be reduced by the addition of small quantities of acid if it exceeds 4.8.

Typically, steps (a) through (c) are performed with the use of less water than is required to achieve the desired final concentrations of (50±5) mg/mL canfosfamide hydrochloride and (100±10) mM sodium citrate, and as a final step (d) water is added to achieve the desired final concentrations. For example, when the aqueous sodium citrate buffer is prepared by adding solid sodium citrate and then citric acid to water, the initial amount of water in which the buffer ingredients are to be dissolved may be (85-95) % of the amount of water needed to achieve the final concentration, allowing for the use of additional water to rinse in the solid ingredients as the formulation is prepared; then, following any necessary pH adjustment, the remaining amount of water is added to achieve the desired final concentrations.

The resulting formulation may be "polish filtered", such as by filtration through a 0.45 μm filter; and is then typically sterile filtered, such as by filtration through a 0.2 μm filter, and the formulation would then be suitable for injection.

The formulation steps are typically performed under inert gas, e.g. under nitrogen purge.

Typically, the formulation will be lyophilized for storage (and subsequent reconstitution before administration), using methods conventional in the art and as illustrated in the following Example, i.e. dispensing into containers of appropriate size, freezing of the formulation in the containers to substantially below 0° C., reduction of pressure to cause removal of the water content of the formulation by sublimation, increase in pressure and temperature, and sealing of the containers.

The quantity per container of the formulation will typically be chosen to permit reconstitution to the same concentration as the original formulation and withdrawal of a convenient amount (e.g. 250 mg or 1 g) of canfosfamide hydrochloride. For 250 mg of canfosfamide hydrochloride, 5.3 mL of the formulation of the first aspect of this invention (a 6% overage) may be lyophilized in a 10 mL vial, allowing for convenient withdrawal of 5.0 mL of formulation after reconstitution with 5.2 mL water; for 1.0 g of canfosfamide hydrochloride, 20.6 mL of the aqueous formulation (a 3% overage) may be lyophilized in a 50 mL vial, allowing for convenient withdrawal of 20.0 mL of the formulation after reconstitution.

EXAMPLE

The following example describes the formulation and lyophilized formulation of this invention, and their preparation. The mixing and filtration operation was conducted under nitrogen purge.

To prepare a 50 L volume of the formulation (density 1.034 Kg/L), 43.5 Kg of water for injection (WFI) was added to a jacketed 80 L stainless steel vessel equipped with a Silverson mixer with a 10 cm stainless steel blade. This was stirred at 800 r.p.m.; 1470 g trisodium citrate dihydrate was added and rinsed in with 1 L of WFI; and stirring was continued for 10 minutes. Citric acid monohydrate, 30.2 g, was added and rinsed in with 500 mL of WFI; and stirring was continued at 1320 r.p.m. for a further 10 minutes. The pH of the solution was measured and adjusted to 6.6 by the addition of two 20 mL increments of 1 M hydrochloric acid, with 5 minutes of stirring at 1320 r.p.m. after each addition. Canfosfamide hydrochloride, 2600 g of 96.8% pure material, was added and rinsed in with 1500 mL of WFI; and stirring was continued for 20 minutes at 2300 r.p.m. and 30 minutes at 2200 r.p.m. The pH of the solution was measured as 4.7. A further 1 Kg of WFI was added and stirred for 10 minutes at 880 r.p.m., after which the solution was cooled to 8° C., giving 50 L of the formulation of the first aspect of this invention, containing 50.3 mg/mL of canfosfamide hydrochloride in 103 mM sodium citrate buffer at pH 4.7.

The formulation was filtered through a 0.45 μm filter and then through two 0.2 μm filters (sterile filtration). The filtered formulation was filled into 10 mL type I glass vials with 5.3 mL fill volume per vial; a 20 mm butyl rubber lyophilization stopper was placed in the lyophilization position on each vial; and the vials were placed onto trays and loaded into the lyophilizer, with the lyophilizer shelves at 5° C. Once the lyophilizer was closed, the lyophilization cycle comprised: hold for 0.6 hours; decrease shelf temperature to −46° C. over 1.7 hours; hold for 5 hours; decrease lyophilizer chamber pressure to 13.3 Pa over 0.8 hours; start nitrogen gas sweep at 12.4 Pa and hold for 5 hours; increase shelf temperature to −25° C. over 1.1 hours; hold for 16.2 hours; increase shelf temperature to 0° C. over 1 hour; hold for 20 hours; increase shelf temperature to 30 C over 1.7 hours; hold for 15 hours; decrease shelf temperature to 8° C. over 0.6 hours; increase lyophilizer chamber pressure to 69 KPa with nitrogen; stopper the vials; increase lyophilizer chamber pressure to atmospheric pressure; open the lyophilizer and unload the stoppered vials. Each vial contained a lyophilized formulation of the second aspect of this invention containing 267 mg canfosfamide hydrochloride and 159 mg trisodium citrate/citric acid. The vials were sealed with an aluminum seal with a flip-off polypropylene cap. When reconstituted with 5.2 mL of WFI, each vial contains 5.3 mL of an aqueous formulation containing 50.3 mg/mL of canfosfamide hydrochloride in 103 mM sodium citrate buffer at pH 4.7; allowing convenient withdrawal of 5.0 mL of the formulation.

An aqueous formulation containing 50 mg/mL of canfosfamide hydrochloride may also be lyophilized in vials of other sizes if a larger unit dose is required, such as 50 mL vials with a fill volume of 20.6 mL, giving a canfosfamide hydrochloride content of 1030 mg (1 g plus 3% overage per vial). The lyophilization cycle may require modification (e.g. lengthening of the cycle time) for larger fill volumes, but such modification will be within the capability of a person of ordinary skill in the art having regard to that skill and this disclosure.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

We claim:

1. A formulation of canfosfamide consisting essentially of (50±5) mg/mL canfosfamide hydrochloride in (100±10) mM aqueous sodium citrate buffer at pH 4.6±0.2.

2. The formulation of claim 1 consisting essentially of 50 mg/mL canfosfamide hydrochloride, 100 mM sodium citrate dihydrate, and 2.9 mM citric acid monohydrate in water, at pH 4.6±0.2.

3. A product consisting essentially of (50±5) mg/mL canfosfamide hydrochloride in (100±10) mM aqueous sodium citrate buffer at pH 4.6±0.2, which product is prepared by a method comprising:
   (a) preparing a sodium citrate buffer at pH 6.5±0.1,
   (b) dissolving the canfosfamide hydrochloride in the buffer, and
   (c) if necessary, adjusting the pH of the resulting solution to pH 4.6±0.2.

4. A product consisting essentially of (50±5) mg/mL canfosfamide hydrochloride in (100±10) mM aqueous sodium citrate buffer at pH 4.6±0.2, which product is prepared by a method comprising:
   (a) preparing a sodium citrate buffer at pH 6.5±0.1,
   (b) dissolving the canfosfamide hydrochloride in the buffer,
   (c) if necessary, adjusting the pH of the resulting solution to pH 4.6±0.2, and
   (d) adding water to achieve the final concentrations.

* * * * *